(12) United States Patent
Reed et al.

(10) Patent No.: US 10,251,901 B2
(45) Date of Patent: Apr. 9, 2019

(54) THERMOSENSITIVE NANOPARTICLE FORMULATIONS AND METHOD OF MAKING THE SAME

(71) Applicant: CELSION CORPORATION, Lawrenceville, NJ (US)

(72) Inventors: Robert A. Reed, Line Lexington, PA (US); Daishui Su, Ellicott City, MD (US)

(73) Assignee: Celsion Corporation, Lawrenceville, NJ (US)

( * ) Notice: Subject to any disclaimer, the term of this patent is extended or adjusted under 35 U.S.C. 154(b) by 0 days.

(21) Appl. No.: 15/364,003

(22) Filed: Nov. 29, 2016

(65) Prior Publication Data

US 2017/0080003 A1 Mar. 23, 2017

Related U.S. Application Data

(62) Division of application No. 13/768,840, filed on Feb. 15, 2013, now abandoned.

(60) Provisional application No. 61/600,418, filed on Feb. 17, 2012.

(51) Int. Cl.
*A61K 9/127* (2006.01)
*A61K 31/704* (2006.01)

(52) U.S. Cl.
CPC .......... *A61K 31/704* (2013.01); *A61K 9/127* (2013.01); *A61K 9/1271* (2013.01); *A61K 9/1278* (2013.01)

(58) Field of Classification Search
CPC .................................................... A61K 9/127
See application file for complete search history.

(56) References Cited

U.S. PATENT DOCUMENTS

| 4,880,635 | A | 11/1989 | Janoff et al. |
| 5,008,380 | A | 4/1991 | Palladino et al. |
| 6,110,491 | A | 8/2000 | Kirpotin |
| 6,214,388 | B1 | 4/2001 | Benz et al. |
| 6,726,925 | B1 | 4/2004 | Needham |
| 2001/0033861 | A1 | 10/2001 | Lasic et al. |
| 2002/0028237 | A1 | 3/2002 | Colbern et al. |
| 2003/0166602 | A1 | 9/2003 | Szoka, Jr. |
| 2005/0142178 | A1 | 6/2005 | Daftary et al. |
| 2006/0222694 | A1 | 10/2006 | Oh et al. |

(Continued)

FOREIGN PATENT DOCUMENTS

JP 2011-502177 A 1/2011
WO WO 2007/024826 A2 3/2007

(Continued)

OTHER PUBLICATIONS

International Search Report and Written Opinion of International Application PCT/US2013/026453, dated Apr. 23, 2013.

(Continued)

*Primary Examiner* — Gollamudi Kishore
(74) *Attorney, Agent, or Firm* — Sterne, Kessler, Goldstein & Fox P.L.L.C.

(57) ABSTRACT

The present invention relates to a formulation of thermosensitive liposomes, and more specifically to a formulation of liposomes comprising phospholipids and a surface active agent, wherein the liposomes support long term storage at temperatures less than or equal to about 8° C., control degradate formation to maximize product potency and release their contents at mild hyperthermic temperatures. Methods of making formulations are also described.

20 Claims, 13 Drawing Sheets

(56) References Cited

U.S. PATENT DOCUMENTS

| | | |
|---|---|---|
| 2007/0269502 A1 | 11/2007 | Pliura et al. |
| 2008/0261913 A1 | 10/2008 | Sommadossi et al. |
| 2009/0117035 A1 | 5/2009 | Needham |
| 2010/0158994 A1 | 6/2010 | Watkin |
| 2010/0239652 A1 | 9/2010 | Rochlitz et al. |
| 2011/0200665 A1 | 8/2011 | Mei et al. |

FOREIGN PATENT DOCUMENTS

| | | |
|---|---|---|
| WO | WO 2009/062399 A1 | 5/2009 |
| WO | WO 2011/109334 A2 | 9/2011 |
| WO | WO 2012/104277 A2 | 8/2012 |

OTHER PUBLICATIONS

De Smet, M., et al., "Temperature-sensitive liposomes for doxorubicin delivery under MRI guidance," *Journal of Controlled Release* 143:120-127, Elsevier B.V., The Netherlands (2010).

Haran, G., et al., "Transmembrane ammonium sulfate gradients in liposomes produce efficient and stable entrapment of amphipathic weak bases," *Biochimica et Biophysica Acta* 1151: 201-215, Elsevier Science Publishers B.V., The Netherlands (1993).

Office Action dated Aug. 19, 2013, in U.S. Appl. No. 13/768,840, Reed, R. et al., filed Feb. 15, 2013, 6 pages.

Office Action dated Nov. 27, 2013, in U.S. Appl. No. 13/768,840, Reed, R. et al., filed Feb. 15, 2013, 9 pages.

Office Action dated Dec. 30, 2014, in U.S. Appl. No. 13/768,840, Reed, R. et al., filed Feb. 15, 2013, 8 pages.

Office Action dated Jul. 22, 2015, in U.S. Appl. No. 13/768,840, Reed, R. et al., filed Feb. 15, 2013, 13 pages.

Office Action dated Sep. 1, 2016, in U.S. Appl. No. 13/768,840, Reed, R. et al., filed Feb. 15, 2013, 13 pages.

Particle Size Distribution for pH-Loaded Formulation

Particle Size Distribution for Ammonium-Loaded Formulation

THERMOSENSITIVE NANOPARTICLE FORMULATIONS AND METHOD OF MAKING THE SAME

FIELD OF THE INVENTION

The present invention relates to a formulation of thermosensitive liposomes, and more specifically to a formulation of liposomes comprising phospholipids and a surface active agent, wherein the liposomes support long term storage at temperatures less than or equal to about 8° C., control degradate formation to maximize product potency and release its contents at mild hyperthermic temperatures. Methods of making formulations are also described.

BACKGROUND OF THE INVENTION

Liposomes are composed of at least one lipid bilayer membrane enclosing an aqueous internal compartment. Liposomes may be characterized by membrane type and by size. Small unilamellar vesicles (SUVs) have a single membrane and typically range between 0.02 and 0.25 μm in diameter; large unilamellar vesicles (LUVs) are typically larger than 0.25 μm. Oligolamellar large vesicles and multilamellar large vesicles have multiple, usually concentric, membrane layers and are typically larger than 0.25 μm. Liposomes with several nonconcentric membranes, i.e., several small vesicles contained within a larger vesicle, are termed multivesicular vesicles.

Liposomes may be formulated to carry therapeutic agents, drugs or other active agents either contained within the aqueous interior space (water soluble active agents) or partitioned into the lipid bilayer (water-insoluble active agents). Liposomes may also be conjugated to an antibody or targeting molecule that permits the delivery of active agent to a specific target site. Encapsulation of a drug in a liposome (1) reduces toxicity of the drug, (2) avoids the body's defenses that normally recognize foreign particles and target them for removal by the reticuloendothelial system (RES) of the liver and spleen, and (3) allows targeting of the drug carrier to the therapeutic site of action, and once there, to release the drug rapidly so that it can act on the target tissue. Further, clearance of the liposome from blood by the cells of the reticuloendothelial system (RES) can be inhibited by incorporating polyethyleneglycol lipids into the liposome membrane; these lipids inhibit the protein adsorption that labels the liposome for RES uptake.

Liposomes can be designed to be not leaky but will become so if a pore occurs in the liposome membrane, or if the membrane becomes fluid (e.g. undergoes a phase transition from a solid or gel phase to a liquid phase), or if the membrane degrades or dissolves. Such a breakdown in permeability can be induced by the application of electric fields (electroporation), or exposure of the liposome to enzymes or surfactants. Another method involves raising the temperature of the membrane to temperatures in the vicinity of its gel to liquid phase transition temperature, where it appears that porous defects at phase boundary regions in the partially liquid and partially solid membrane allow for increased transport of water, ions and small molecules across the membrane. The clinical elevation of temperature in the body is called hyperthermia. This procedure has been used to raise the temperature at a target site in a subject and if temperature-sensitive liposomes can be delivered to the target site then this increase in temperature can trigger the release of liposome contents, giving rise to the selective delivery and release of therapeutic agents at the target site, as initially described by Yatvin et al., *Science* 204:188 (1979). This technique is limited, however, to conditions where the phase transition temperature of the liposome is higher (greater than 37° C.) than the normal tissue temperature.

Hyperthermia causes multiple biologic changes. For a review refer to Issels R D. Hyperthermia adds to Chemotherapy, *European J of Cancer* (2008) 44:2546-2554. Temperatures in the mild hyperthermia range (39-44° C.) mediate localized physiological changes such as increases in blood flow, vasculature permeability and tissue oxygenation. The vasculature supporting solid tumors is chaotic in structure and the endothelial cells lining the micro-vasculature do not seal together normally resulting in a porous quality. Hyperthermia causes an increase in the pore size in the abnormal tumor microvasculature and therefore enhances the extravasation of nanoscale molecules, such as liposomes of about 100 nm diameter, into the tumor interstitium (Bates D A, Mackillop W J. Hyperthermia, adriamycin transport, and cytotoxicity in drug-sensitive and -resistant Chinese hamster ovary cells, *Cancer Res* (1986) 46:5477-5481; Nagaoka S, Kawasaki S, Sasaki K, Nakanishi T. Intracellular uptake, retention and cytotoxic effect of adriamycin combined with hyperthermia in vitro. *Jpn J Cancer Res* (1986) 77:205-211). For these reasons mild hyperthermia is selectively lethal to tumor cells, with the antitumor effect increasing as the temperature increases.

Heat sensitive liposomes carry a high concentration of chemotherapeutic agent to solid tumors and the supporting vasculature and release drug locally when heated. Hyperthermia selectively increases liposomal uptake, liposomal permeability, stimulates localized drug release, increases the influx of drug into tumor cells, and increases drug binding to tumor cell DNA (the latter being essential to the mechanism of action of a number of chemotherapeutic agents).

In order to begin to use hyperthermia for the treatment of deep-seated tumors (e.g., prostate, ovarian, colorectal and breast tumors), it is accordingly desirable to devise liposome formulations capable of delivering therapeutic amounts of active agents in response to mild hyperthermic conditions, i.e., for clinically attainable temperatures in the range 39-45° C.

U.S. Pat. No. 6,726,925 describes liposomes that are sensitive to alterations in the temperature of the surrounding environment. The liposomes are loaded with, inter alia, doxorubicin, an approved and frequently used oncology drug for the treatment of a wide range of cancers. The doxorubicin containing liposomal formulation is administered intravenously and in combination with hyperthermia can provide local tumor control and improve quality of life. Localized mild hyperthermia (39.5-45 degrees Celsius) releases the entrapped doxorubicin from the liposome. This delivery technology enables high concentrations of doxorubicin to be deposited preferentially in a targeted tumor. U.S. Pat. No. 7,901,709 describes a method for heat-activated liposomal encapsulation of doxorubicin.

Published International Application No. WO 2007/024826 describes a method of storing a liposome or nanoparticle formulation including freezing such a formulation. The formulation describes a method of storing liposomes having enhanced stability and storage characteristics.

Key design principles that are required for a hyperthermically activated liposomal-drug formulation to be effective are: 1) near complete encapsulation of active agent to allow the drug to be associated with the liposome in the systemic circulation, 2) a membrane that is engineered to retain drug at normal body temperatures (37° C.) and release drug at mild hyperthermia temperatures (i.e. 41-43° C.), 3) a membrane composition and particle size that allows the liposome to remain in the systemic circulation long enough to allow the application of a heating modality to trigger the release of the drug to its target, and 4) liposome size that permits its extravasation from the blood stream across leaky tumor micro-vasculature permitting targeting of chemotherapeutic drugs to a tumor site.

An additional important design issue discovered by the inventors with liposomal formulations of doxorubicin (e.g. disclosed in U.S. Pat. No. 7,901,709) is the stabilizing effect of doxorubicin complex (co-crystal or salt) formation on the stability of the finished drug product. Successful control of degradation rates will result in significant impact on the storage temperature and long term stability of the drug product. Two degradation products of interest are 8-desacetyl-8-carboxy daunorubicin and impurity A.

The present invention solves a persistent problem with drug degradation in doxorubicin liposomal formulation that results in a citrate complex (co-crystal or salt). It has been found that the citrate complex plays a significant role in doxorubicin instability and formation of degradates. More specifically, the formation of 8-desacetyl-8-carboxy daunorubicin and impurity A can be significantly reduced by changing the formation of a citrate complex to a sulfate complex (co-crystal or salt). In addition, the present invention maintains the key design principles listed above for an efficacious hyperthermically activated liposomal formulation containing an active agent.

BRIEF SUMMARY OF THE INVENTION

In one aspect, the invention provides a pharmaceutical composition, comprising a suspension of liposomes having a gel-phase lipid bilayer and doxorubicin entrapped inside the liposomes; said lipid bilayer comprising:
  (i) one or more phospholipids selected from the group consisting of phosphatidyl cholines, phosphatidyl glycerols, phosphatidyl inositols, and phosphatidyl ethanolamines;
  (ii) one or more phospholipids derivatized with a hydrophilic polymer; and
  (iii) one or more lysolipids selected from the group consisting of monoacylphosphatidyl cholines, monoacylphosphatidylglycerols, monoacylphosphatidylinositols, and monoacylphosphatidylethanolamines;
wherein the lipid bilayer constituents are provided in a molar ratio (i):(ii):(iii) of about 80-90:2-8:2-18; wherein the liposomes in the suspension have an average particle size of between about 50 and about 150 nm; and
wherein the relative concentration of impurity A after 6 months of storage at about less than or equal to 8° C. is less than 0.5%, and wherein impurity A is a peak with a relative retention time of about 1.4 when separation is achieved using high performance liquid chromatography (HPLC) with a C18 reverse phase column and acetic acid/methanol solvent gradient elution buffer.

In another aspect, the invention provides a method for loading doxorubicin into temperature sensitive liposomes, comprising:
(a) preparing a suspension of liposomes having a gel-phase lipid bilayer and a greater concentration of ammonium ions inside the liposomes than outside the liposomes, said lipid bilayer comprising:
  (i) one or more phospholipids selected from the group consisting of phosphatidyl cholines, phosphatidyl glycerols, phosphatidyl inositols, and phosphatidyl ethanolamines;
  (ii) one or more phospholipids derivatized with a hydrophilic polymer; and
  (iii) one or more lysolipids selected from the group consisting of monoacylphosphatidyl cholines, monoacylphosphatidylglycerols, monoacylphosphatidylinositols, and monoacylphosphatidylethanolamines;
  wherein the lipid bilayer constituents are provided in a molar ratio (i):(ii):(iii) of about 80-90:2-8:2-18; and
  where said preparing includes reducing the size of the liposomes in the suspension to an average particle size of between about 50 and about 150 nm;
(b) adding a doxorubicin solution to the suspension of liposomes, wherein the doxorubicin is taken up into the liposomes.

In another aspect, the invention comprises a liposomal preparation made by the method set forth above.

In another aspect, the invention comprises a liposomal preparation comprising doxorubicin and an imaging agent. In yet another aspect, the invention comprises a liposomal preparation comprising doxorubicin and another drug.

These and other aspects and advantages of the invention are set forth in detail hereinbelow.

BRIEF DESCRIPTION OF THE DRAWINGS/FIGURES

FIG. 1 schematically represents a liposome having a bilayer membrane containing dipalmitoylphosphatidylcholine (DPPC) as a phospholipid, 1,2-distearoyl-sn-glycero-3-phosphoethanolamine-N-[poly(ethyleneglycol) 2000 (DSPE-MPEG), and monosteroyl-phosphatidylcholine (MSPC) as a lysolipid. The orientation of the lysolipid monomers and their presence in both the inner and outer layers of the lipid bilayer is indicated.

Figure 9A:
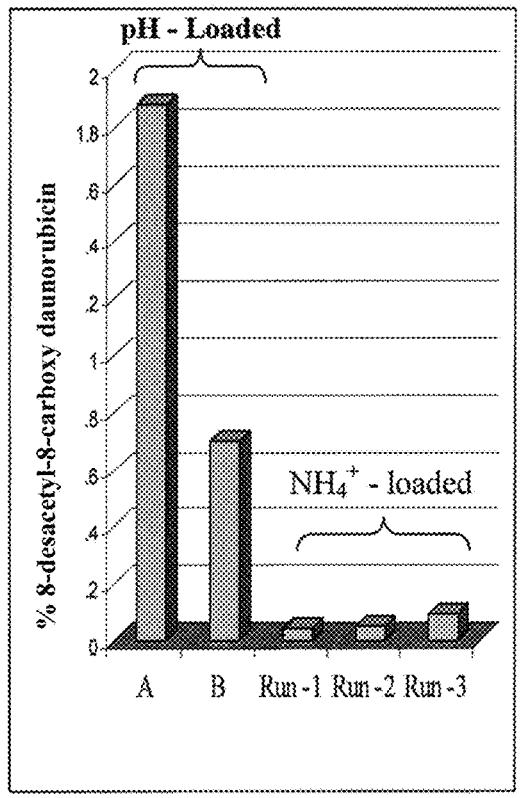
Figure 9B:
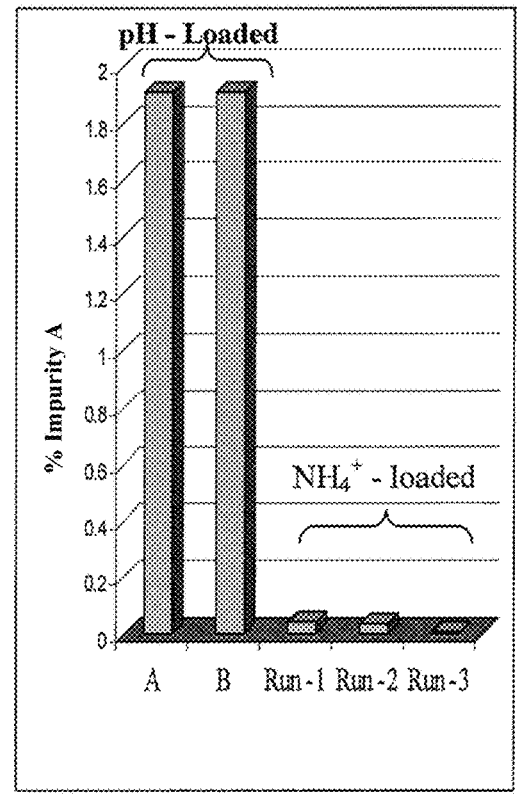

FIG. 9a shows a comparison of the levels of 8-desacetyl-8-carboxy daunorubicin in the pH-loaded and $NH_4^+$-loaded doxorubicin liposomes. FIG. 9b shows a comparison of the levels of Impurity A in the pH loaded or $NH_4^+$-loaded doxorubicin liposomes. The "A" and "B" bars denote impurity levels for a formulation prepared using excipients sourced from different suppliers. FIG. 9a and FIG. 9b also show the levels of impurities 8-desacetyl-8-carboxy daunorubicin and impurity A for three replicate runs of NH$_4^+$-loaded doxorubicin liposomes prepared according to the present invention.

Figure 10:
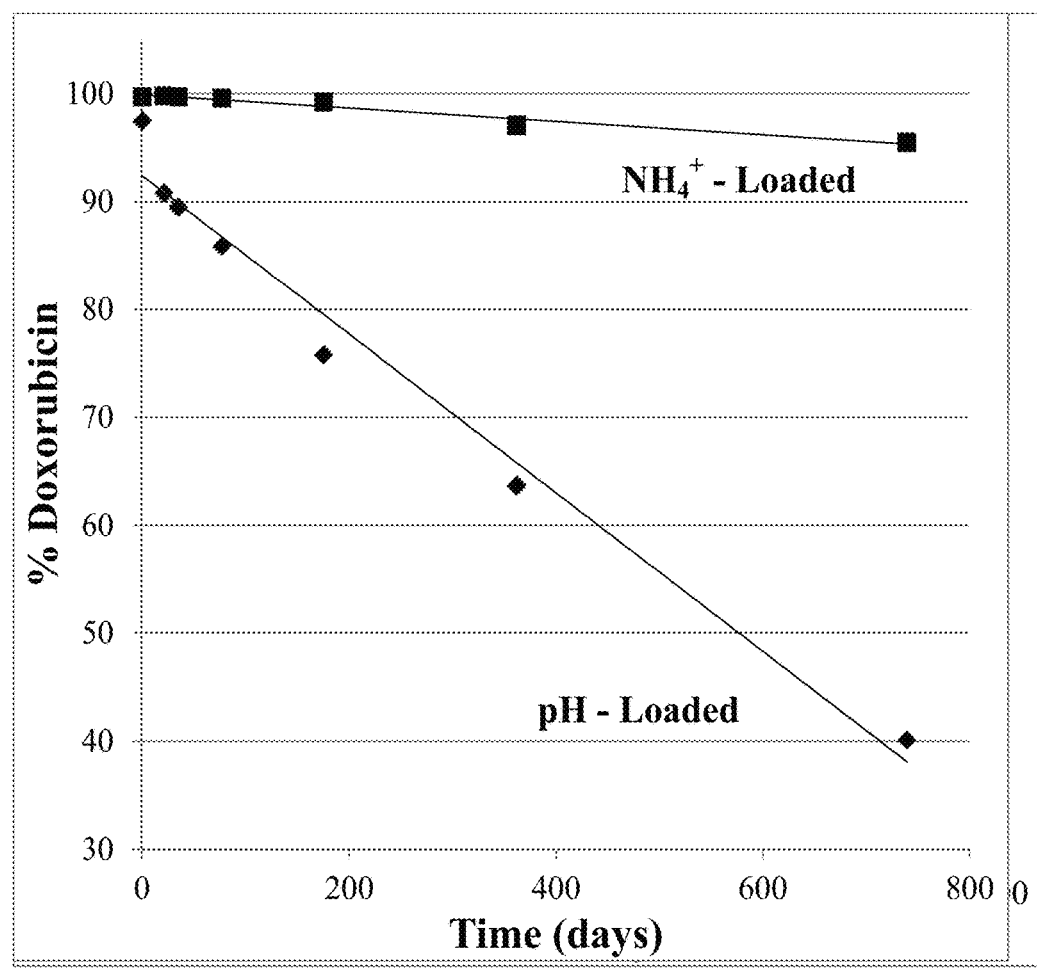

FIG. 10 shows the levels of doxorubicin in pH-loaded and NH$_4^+$-loaded doxorubicin liposomes upon storage for prolonged periods of time at 2-8° C.

Figure 11:
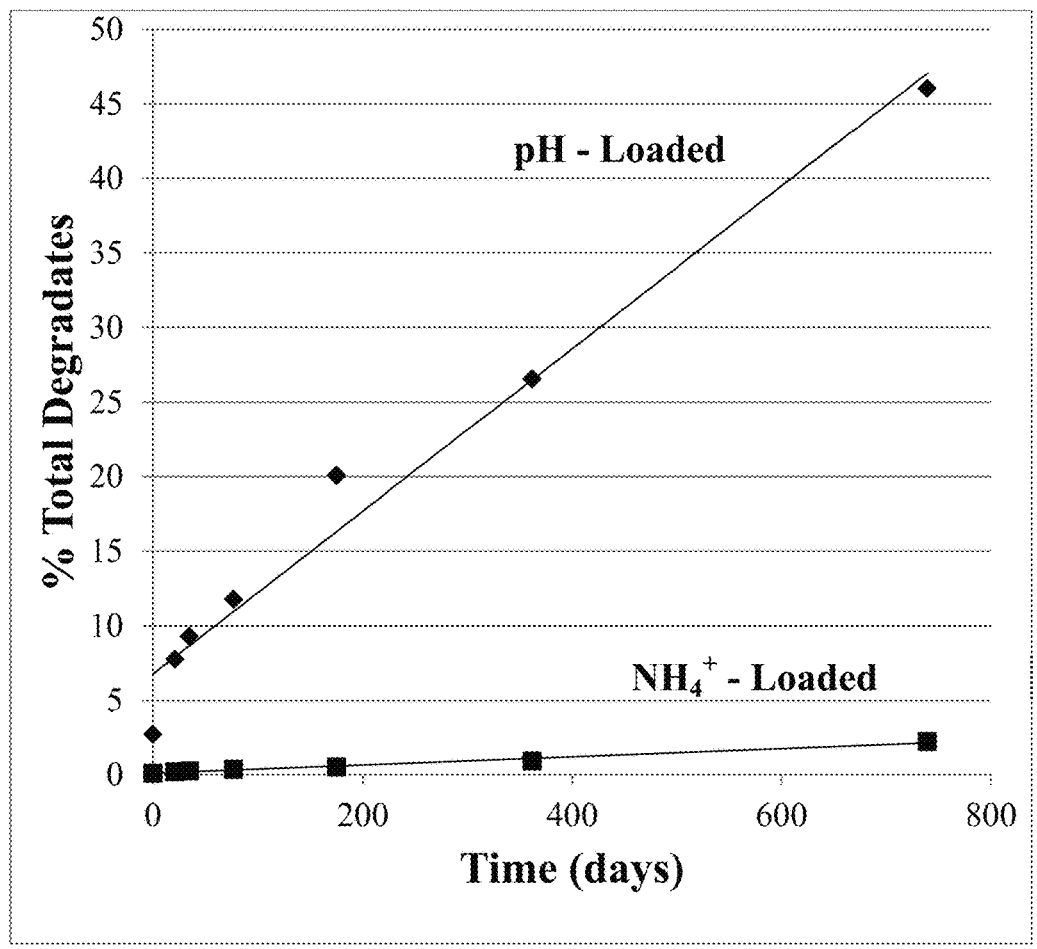

FIG. 11 shows the levels of degradate growth in pH-loaded and NH$_4^+$-loaded doxorubicin liposomes upon storage for prolonged periods of time at 2-8° C.

Figure 12:
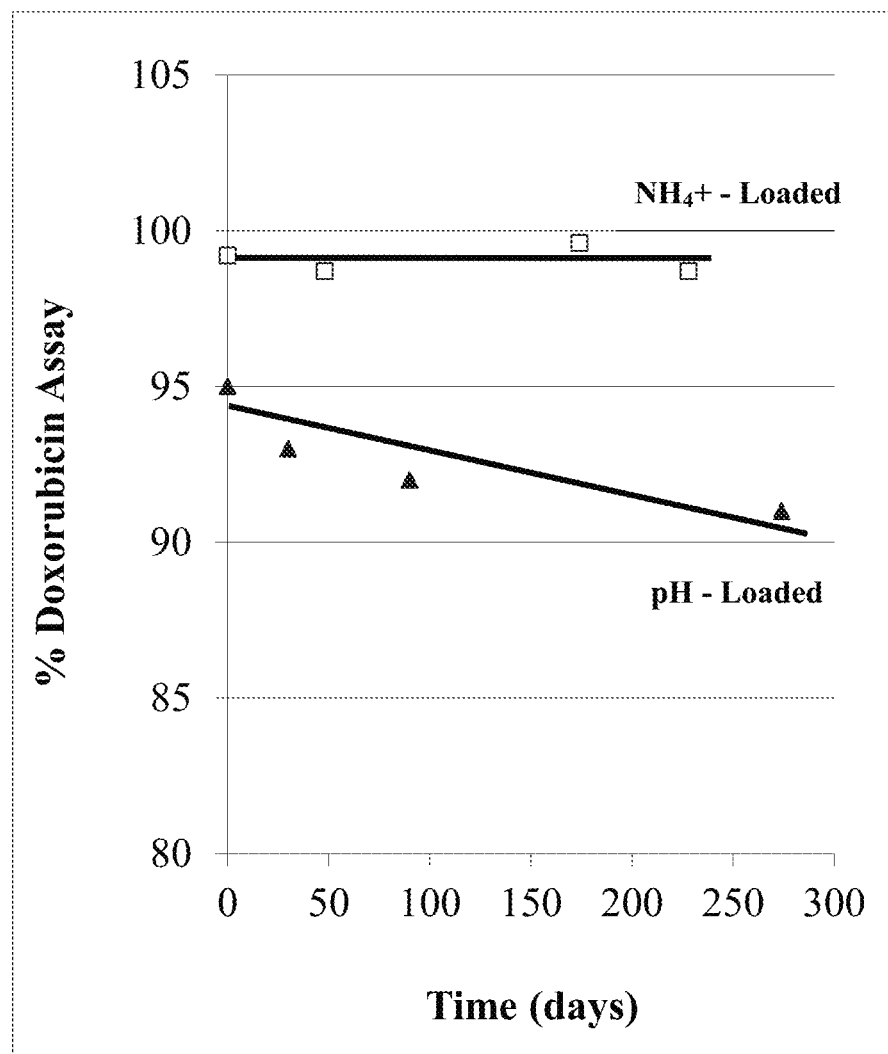

FIG. 12 shows the levels of doxorubicin in pH-loaded and NH$_4^+$-loaded doxorubicin liposomes upon storage for prolonged periods of time at −20° C.

Figure 13:
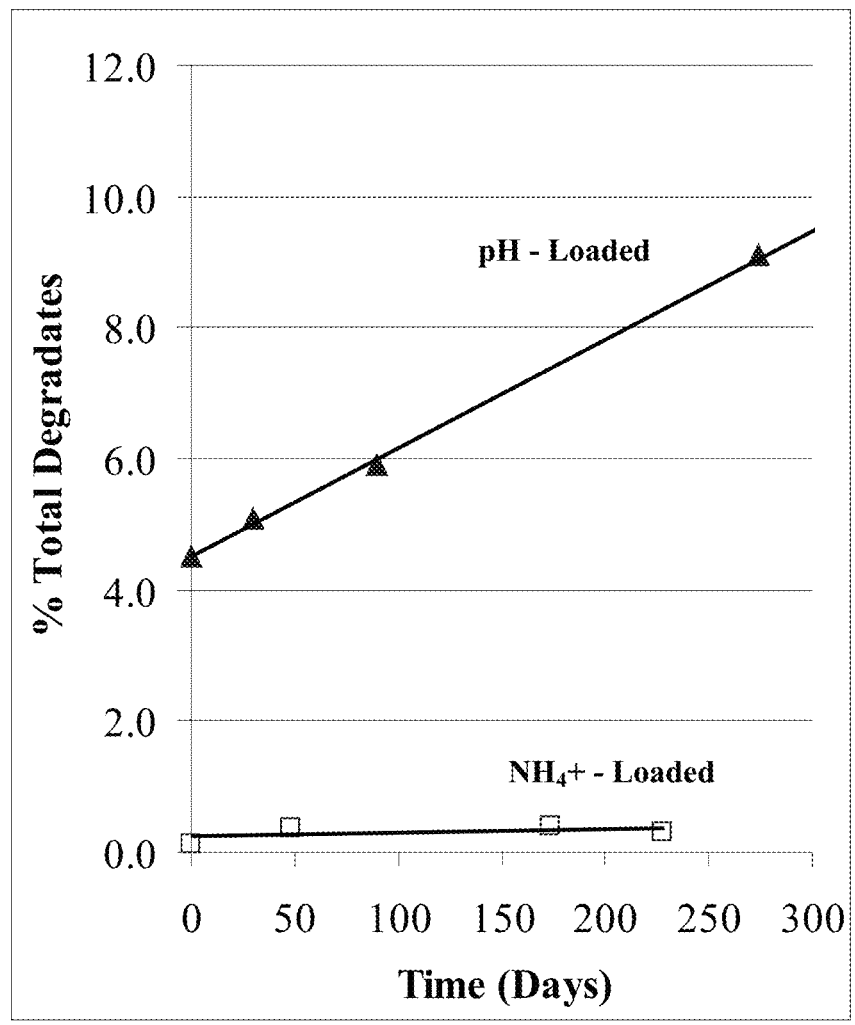

FIG. 13 shows the levels of degradate growth in pH-loaded and NH$_4^+$-loaded doxorubicin liposomes upon storage for prolonged periods of time at −20° C.

DETAILED DESCRIPTION OF THE INVENTION

The present invention will now be described in reference to embodiments set forth herein and in the figures. These embodiments are merely for the purposes of illustration and are not to be interpreted as limiting the invention as defined by the claims.

In one aspect, the invention provides a liposomal preparation, comprising a suspension of liposomes having a gel-phase lipid bilayer and an active agent entrapped inside the liposomes; said lipid bilayer comprising:
(i) one or more phospholipids selected from the group consisting of phosphatidyl cholines, phosphatidyl glycerols, phosphatidyl inositols, and phosphatidyl ethanolamines;
(ii) one or more phospholipids derivatized with a hydrophilic polymer; and
(iii) one or more lysolipids selected from the group consisting of monoacylphosphatidyl cholines, monoacylphosphatidylglycerols, monoacylphosphatidylinositols, and monoacylphosphatidylethanolamines;
wherein the active agent is selected from the group consisting of doxorubicin, bleomycin, dacarbazine, daunorubicin, dactinomycin, fludarabine, gemcitabine, idarubicin, methotrexate, mitomycin, mitoxantrone, vinblastine, vinorelbine, and vincristine, and wherein the lipid bilayer constituents are provided in a molar ratio of about 80-90:2-8:2-18; and wherein the size of the liposomes in the suspension is between about 50 and about 150 nm.

In one embodiment, the active agent is doxorubicin, and the relative concentration of impurity A after 6 months of storage at less than or equal to 8° C. is less than 0.5%, wherein impurity A is a peak with a relative retention time approximately 1.4 in a high performance liquid chromatography (HPLC) with a C18 reverse phase column with an acetic acid/methanol solvent gradient elution conditions.

In one embodiment, the relative concentration of impurity A after 6 months of storage at less than or equal to 8° C. is less than about 0.5%, or less than 0.4%, or less than 0.3%, or less than 0.2%. In another embodiment, the relative concentration of impurity A after about 1 year of storage at less than or equal to 8° C. is less than about 0.5%, or less than 0.4%, or less than 0.3%, or less than 0.2%. In another embodiment, the relative concentration of impurity A after about 2 years of storage at less than or equal to 8° C. is less than about 1%, 0.75%, 0.5%, or less than 0.4%, or less than 0.3%, or less than 0.2%.

In one embodiment, the relative concentration of 8-desacetyl-8-carboxy daunorubicin after 6 months of storage at less than or equal to 8° C. is less than about 0.5%, less than 0.4%, less than 0.3%, or less than 0.2%. In another embodiment, the relative concentration of 8-desacetyl-8-carboxy daunorubicin after about 1 year of storage at less than or equal to 8° C. is less than about 0.5%, less than 0.4%, less than 0.3%, or less than 0.2%. In another embodiment, the relative concentration of 8-desacetyl-8-carboxy daunorubicin after about 2 years of storage at less than or equal to 8° C. is less than about 2.0%, less than 1.6%, less than 1.5%, less than 1.0%, less than 0.5%, less than 0.4%, less than 0.3%, or less than 0.2%.

In a further embodiment, the concentration of doxorubicin after 150 days of storage at a temperature of about less than or equal to 8° C. is greater than 95%, greater than 96%, greater than 97%, greater than 98%, greater than 99%, or greater than 99.5%, of the initial doxorubicin concentration, as determined by HPLC with a C18 reverse phase column with an acetic acid/methanol solvent gradient elution conditions. In another embodiment, the concentration of doxorubicin after about six months of storage at a temperature of about less than or equal to 8° C. is greater than 95%, greater than 96%, greater than 97%, greater than 98%, greater than 99%, or greater than 99.5%, of the initial doxorubicin concentration, as determined by HPLC with a C18 reverse phase column with an acetic acid/methanol solvent gradient elution conditions. In another embodiment, the concentration of doxorubicin after about one year of storage at a temperature of about less than or equal to 8° C. is greater than 95%, greater than 96%, greater than 97%, greater than 98%, greater than 99%, or greater than 99.5%, of the initial doxorubicin concentration, as determined by HPLC with a C18 reverse phase column with an acetic acid/methanol solvent gradient elution conditions. In another embodiment, the concentration of doxorubicin after about two years of storage at a temperature of about less than or equal to 8° C. is greater than 95%, greater than 96%, greater than 97%, greater than 98%, greater than 99%, or greater than 99.5%, of the initial doxorubicin concentration, as determined by HPLC with a C18 reverse phase column with an acetic acid/methanol solvent gradient elution conditions.

In another embodiment, the invention is a pharmaceutical composition, wherein the formation of total degradation products after 150 days of storage at a temperature of about less than or equal to 8° C. is less than 1%, or less than 0.5%. In a further embodiment, the invention is a pharmaceutical composition, wherein the formation of total degradation products after about six months of storage at a temperature of about less than or equal to 8° C. is less than 1%, or less than 0.5%. In a further embodiment, the invention is a pharmaceutical composition, wherein the formation of total degradation products after about one year of storage at a temperature of about less than or equal to 8° C. is less than 1%, or less than 0.5%. In a further embodiment, the invention is a pharmaceutical composition, wherein the formation of total degradation products after about two years of storage at a temperature of about less than or equal to 8° C. is less than 2.5%, less than 1%, or less than 0.5%.

In yet another embodiment, the liposomes are suspended in a buffer comprising a saccharide. The saccharide may be a monosaccharide, or a disaccharide, such as sucrose or lactose. In another embodiment, the buffer further comprises histidine.

In another aspect, the invention provides a method for loading an active agent into temperature sensitive liposomes, comprising:

(a) preparing a suspension of liposomes having a gel-phase lipid bilayer and a greater concentration of ammonium ions inside the liposomes than outside the liposomes, said lipid bilayer comprising:
  (i) one or more phospholipids selected from the group consisting of phosphatidyl cholines, phosphatidyl glycerols, phosphatidyl inositols, and phosphatidyl ethanolamines;
  (ii) one or more phospholipids derivatized with a hydrophilic polymer; and
  (iii) one or more lysolipids selected from the group consisting of monoacylphosphatidyl cholines, monoacylphosphatidylglycerols, monoacylphosphatidylinositols, and monoacylphosphatidylethanolamines;
  wherein the lipid bilayer constituents are provided in a molar ratio (i):(ii):(iii) of about 80-90:2-8:2-18; and
  where said preparing includes reducing the size of the liposomes in the suspension to an average particle size of between about 50 and about 150 nm;
(b) adding a solution of the active agent to the suspension of liposomes, wherein the active agent is taken up into the liposomes,
  wherein the active agent is selected from the group consisting of doxorubicin, bleomycin, dacarbazine, daunorubicin, dactinomycin, fludarabine, gemcitabine, idarubicin, methotrexate, mitomycin, mitoxantrone, vinblastine, vinorelbine, and vincristine.

In one embodiment, the active agent is doxorubicin. In one embodiment, at least 90%, at least 91%, at least 92%, at least 93%, at least 94%, at least 95%, at least 96%, at least 97%, or at least 98% of the doxorubicin present in the solution is taken up into the liposomes.

In another embodiment, the concentration of doxorubicin taken up into the liposomes is about 1 mM to about 200 mM, preferably about 10 to about 65 mM, and most preferably about 45 mM to about 55 mM. In a further embodiment, the concentration of doxorubicin taken up into the liposomes is about 50 mM. In another embodiment, the concentration of doxorubicin taken up into the liposomes is about 75 mM.

Liposomes of the present invention are composed of phospholipids selected from the group consisting of phosphatidyl cholines, phosphatidyl glycerols, phosphatidyl inositols, and phosphatidyl ethanolamines. The phospholipids preferably possess a solid or gel form to liquid transition temperature in the lower end of the hyperthermic range (e.g., the range of from approximately 38° C. to approximately 45° C.). More preferred are phospholipids whose acyl groups are saturated. In one embodiment, the one or more phospholipids have two same or different $C_{14}$-$C_{20}$ acyl groups, such as, for example dipalmitoylphosphatidylcholine (DPPC), distearoylphosphatidyl glycerol (DSPG), or a combination thereof.

The liposomes of the present invention are composed of one or more lysolipids. In one embodiment, the lysolipid is monopalmitoylphosphatidylcholine (MPPC), monolaurylphosphatidylcholine (MLPC), monomyristoylphosphatidylcholine (MMPC), monostearoylphosphatidylcholine (MSPC), or a mixture thereof.

In one embodiment of the invention, the total concentration of lipids in the final liposomal formulation is about 10-50 mg/ml, about 20-50 mg/ml, about 30-40 mg/ml, about 20 mg/ml, about 30 mg/ml, or 40 mg/ml. In another embodiment, the concentration of doxorubicin in the liposomal formulation is about 0.2-40 mg/ml, about 0.5-30 mg/ml, about 1-20 mg/ml, about 2-10 mg/ml, about 1 mg/ml, about 2 mg/ml, about 3 mg/ml, about 4 mg/ml or about 5 mg/ml. In one embodiment of the invention the doxorubicin to lipid ratio is 0.02-10, about 0.05, about 1, about 2, about 3, about 4, about 5, about 6, about 7, about 8, about 9 or about 10.

Liposomes of the present invention include polymer-derivatized lipids to decrease liposome uptake by the RES and thus increase the circulation time of the liposomes. Suitable polymers include hydrophilic polymers such as polyethylene glycol, polyvinylpyrolidine, olylactic acid, polyglycolic acid, copolymers of polylactic acid and polyglycolic acid, polyvinyl alcohols, polyvinylpyrrolidone, dextrans, oligosaccharides, along with mixtures of the above. In one embodiment, the one or more phospholipids derivatized with a hydrophilic polymer is a polyethylene glycol derivatized (PEGylated) lipid. Preferably, the PEGylated lipid is 1,2-distearoyl-sn-glycero-3-phosphoethanolamine-N-[poly(ethyleneglycol) 2000].

In one embodiment, the invention provides a method for loading a liposome with an active agent which is bleomycin, dacarbazine, daunorubicin, dactinomycin, fludarabine, gemcitabine, idarubicin, methotrexate, mitomycin, mitoxantrone, vinblastine, vinorelbine, or vincristine.

In one embodiment, the said preparing comprises preparing the liposomes in the presence of an ammonium salt, provided as an ammonium sulfate solution. In one embodiment, the concentration of ammonium sulfate in the solution is about 100 mM to about 300 mM, preferably about 200 mM.

In another embodiment, the ammonium salt is provided as a salt of adipic acid, L-ascorbic acid, L-aspartic acid, citric acid, fumaric acid, glutamic acid, glutaric acid, hippuric acid, hydrochloric acid, D,L-lactic acid, maleic acid, L-malic acid, phosphoric acid, succinic acid, or L-tartaric acid. In a further embodiment, the ammonium salt in the solution is about 100 mM to about 300 mM, preferably about 200 mM.

The ammonium ions outside the liposomes are replaced with a monosaccharide or disaccharide solution. In a further embodiment, the concentration of the monosaccharide or disaccharide solution is about 5-15%, preferably about 10%. This replacement or exchange can be carried out by techniques such as dialysis or diafiltration.

In a further embodiment, the ammonium ions outside the liposomes are replaced with a monosaccharide solution. In another embodiment, the ammonium ions outside the liposomes are replaced with a disaccharide solution, such as for example, a sucrose or a lactose solution.

In one embodiment, a histidine buffer is added to the liposomal preparation before step (b). In a further embodiment, the concentration of the histidine buffer is about 5 mM to about 15 mM, preferably about 10 mM.

A method of preparing a liposomal formulation according to the present invention comprises mixing the bilayer components in the appropriate proportions in a suitable organic solvent. Useful solvents include chloroform, acetone, methanol or methylene chloride. The solvent is then evaporated to form a dried lipid film. The film is rehydrated (at temperatures above the phase transition temperature of the lipid mixture) using an aqueous solution containing an equilibrating amount of the lysolipid and a desired active agent, e.g., doxorubicin. The liposomes formed after rehydration are extruded to form liposomes of a desired size. For example, when liposomes composed of 80:20 DPPC:MSPC are produced, rehydration is carried out at a temperature above the phase transition temperature of this particular lipid mixture (above 39° C.). The aqueous solution used to rehydrate the lipid film comprises an equilibrating amount of lysolipid monomers (e.g., a concentration equal to the Critical Micelle Concentration of MSPC, about 1 micromolar).

Description of Proposed Manufacturing Process and Controls

Figure 1:
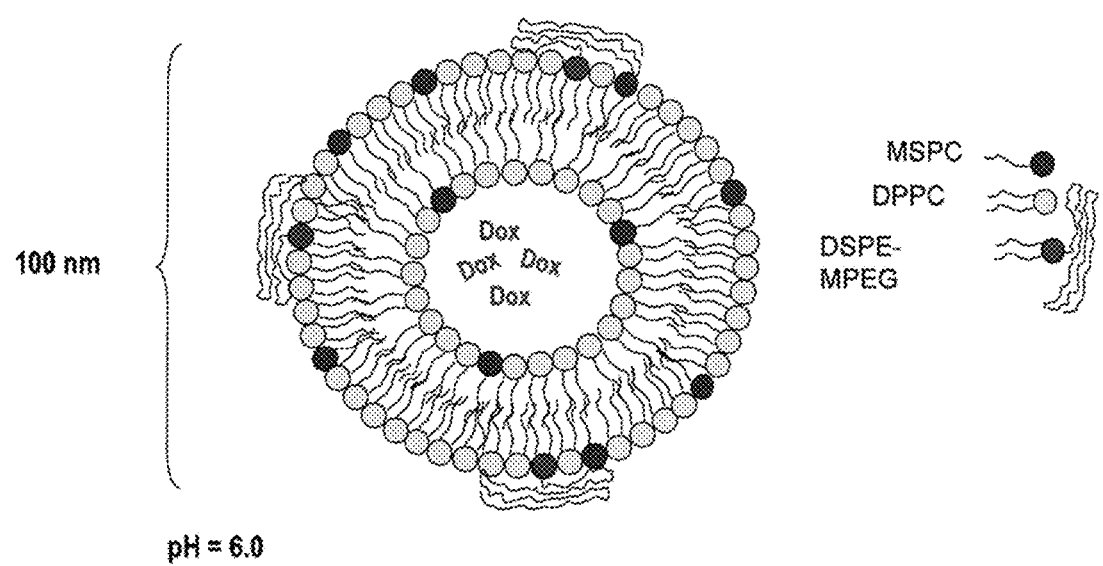
Figure 2:
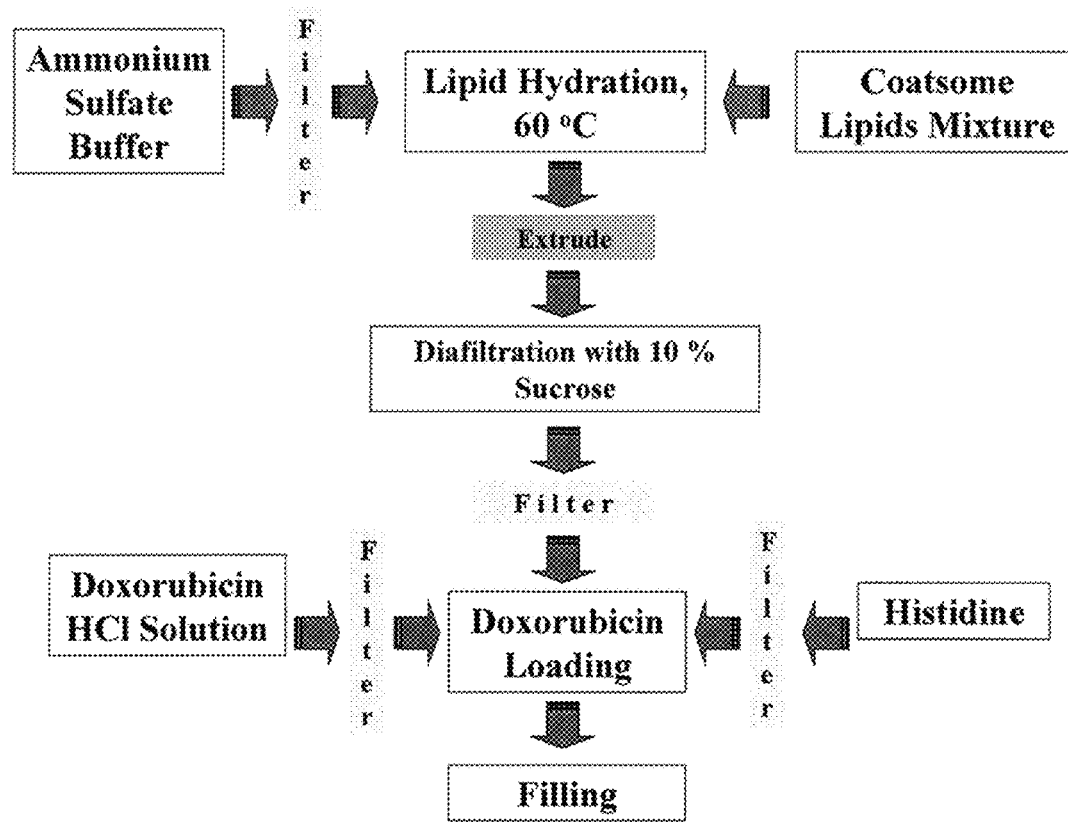
FIG. 2 is a schematic representation of the ammonium loaded doxorubicin liposomes manufacturing process.

The manufacturing process for large scale batches of the ammonium loaded formulation is described below. The process can be employed to produce various size batches of formulation, for example, a 2-2000 L scale batch. A proposed manufacturing process is illustrated schematically in FIG. 2.

Stepwise manufacturing process:
1. Prepare an ammonium sulfate buffer by dissolving appropriate quantities of ammonium sulfate in water for injection (WFI) followed by a bioburden reduction filtration. The molarity of the buffer may be, for example, 200 mM.
2. Hydrate the lipids utilizing the ammonium sulfate buffer from Step 1 for an appropriate amount of time at an elevated temperature (45-70° C.). For example, the lipids are hydrated for 1 hour at 60° C.
3. Extrude the hydrated lipid mixture through filter membranes having a certain pore size at an elevated temperature, in order to obtain liposomes of desired size. For example, the hydrated lipid mixture is extruded through 80 nm polycarbonate filter membranes at 65° C. to form ~100 nm liposomes.
4. Exchange the non-liposome entrapped ammonium sulfate against a saccharide solution, for example a 10% sucrose solution, followed by sterile filtration through a preheated filter, such as a Sartobran P filter.
5. Prepare a histidine HCl buffer, for example, a 100 mM histidine buffer at pH 6, by dissolving appropriate quantities of histidine HCl in WFI, followed by sterile filtration.
6. Prepare a doxorubicin HCl solution, for example at a concentration of 5.0 mg/mL, by dissolving appropriate quantity of doxorubicin HCl in WFI, followed by sterile filtration.
7. Mix 1.0 parts sterile liposome with 0.8 parts sterile doxorubicin HCl solution, and incubate at 35° C. for 4 hours.
8. Add 0.2 parts sterile histidine buffer and mix well.

In one embodiment, the invention is a liposomal preparation made by a method for loading doxorubicin into temperature sensitive liposomes, comprising:
(a) preparing a suspension of liposomes having a gel-phase lipid bilayer and a greater concentration of ammonium ions inside the liposomes than outside the liposomes, said lipid bilayer comprising:
  (i) one or more phospholipids selected from the group consisting of phosphatidyl cholines, phosphatidyl glycerols, phosphatidyl inositols, and phosphatidyl ethanolamines;
  (ii) one or more phospholipids derivatized with a hydrophilic polymer; and
  (iii) one or more lysolipids selected from the group consisting of monoacylphosphatidyl cholines, monoacylphosphatidylglycerols, monoacylphosphatidylinositols, and monoacylphosphatidylethanolamines;
  wherein the lipid bilayer constituents are provided in a molar ratio (i):(ii):(iii) of about 80-90:2-8:2-18; and
  where said preparing includes reducing the size of the liposomes in the suspension to an average particle size of between about 50 and about 150 nm;
(b) adding a doxorubicin solution to the suspension of liposomes, wherein the doxorubicin is taken up into the liposomes.

Liposomes of between 0.05 to 0.3 microns in diameter, have been reported as suitable for tumor administration (U.S. Pat. No. 5,527,528 to Allen et al.). Sizing of liposomes according to the present invention may be carried out according to methods known in the art, and taking into account the active agent contained therein and the effects desired (see, e.g., U.S. Pat. No. 5,225,212 to Martin et al; U.S. Pat. No. 5,527,528 to Allen et al., the disclosures of which are incorporated herein by reference in their entirety). In a preferred embodiment of the present invention, liposomes are from about 0.05 microns or about 0.1 microns in diameter, to about 0.3 microns or about 0.4 microns in diameter. Liposome preparations may contain liposomes of different sizes. Advantageously, these liposomes comprise lipid mixtures set forth herein and are therefore temperature-sensitive, with an ability to release contained drug, as described.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the average sizes of liposomes produced by extrusion through that membrane. See e.g., U.S. Pat. No. 4,737,323.

In another preferred embodiment of the present invention, liposomes are from about 50 nm, 100 nm, 120 nm, 130 nm, 140 nm or 150 nm, up to about 175 nm, 180 nm, 200 nm, 250 nm, 300 nm, 350 nm, 400 nm or 500 nm in diameter.

In one embodiment, the liposomal preparation of the present invention is stored at a temperature of less than or equal to 8° C., from about 2° C. to about 8° C., from about −80° C. to about −15° C., from about −30° C. to about −15° C., or from about −15° C. to about 2° C.

In another aspect, the liposomal preparation comprises doxorubicin and an imaging or diagnostic agent. The ability to encapsulate an imaging agent in a liposome or an imaging agent in combination with a therapeutic is desirable for a number of reasons. First, the therapeutic efficacy of the active agent will be increased with the ability to visualize release of the imaging agent and thus infer the release of drug. This would provide the tools to determine the drug's tissue penetration and concentration. Further, combining a drug with an imaging agent in a liposome will permit monitoring and quantitation of drug release over time, tissue distribution, and drug clearance. Secondly, a liposome carrying and releasing imaging agent will allow for the opportunity to pre-screen patients. For example, a select patient population may be identified as likely to benefit from the therapeutic liposome based on the "leakiness" of tumor vasculature. This leakiness, as visualized using an imaging agent, is an indicator of ability of the active agent to extravasate across the microvasculature and any fibrotic tissue to access and treat the tumor. Examples of imaging or diagnostic agents that may be employed include, but are not limited to, agents for X-ray imaging, magnetic resonance imaging (MRI), ultrasound imaging or nuclear medicine imaging.

In X-ray imaging, including applications such as computed tomography (CT) and digital subtraction angiography (DSA), contrast is based on differences in electron density. In one aspect of the invention, the liposomal preparation comprises doxorubicin and an X-ray contrast agent. X-ray contrast agents are generally based on heavy elements, and include barium salts such as barium sulphate, which may be used to enhance visualization of the gastrointestinal system and iodinated contrast agents, which may be used in visualization of the gastrointestinal system and in parenteral studies. Iodinated X-ray contrast agents include, but are not limited to, iohexol, iopentol, iopamidol, iodixanol, iopromide, iotrolan, metrizamide, metrizoic acid, diatriazoic acid, iothalamic acid, ioxaglic acid and salts of these acids.

In another aspect of the invention, the liposomal preparation comprises doxorubicin and an MRI contrast agent. MRI contrast agents include paramagnetic chelates, for example based on manganese (2+), gadolinium (3+) or iron (3+). Hydrophilic chelates such as GdDTPA, GdDOTA, GdHPDO3A and GdDTPA-BMA are distributed extracellularly and eliminated renally. Such compounds are useful in, for example, visualizing lesions in the central nervous system. Other more organ- or tissue-specific agents include MnDPDP, GdBOPA, GdEOB-DTPA, paramagnetic porphyrins, macromolecular compounds, particles and liposomes.

In yet another aspect of the invention, the liposomal preparation comprises doxorubicin and an ultrasonic imaging agent. Ultrasonic imaging is based on penetration of ultrasound waves, e.g. in the frequency range 1-10 MHz, into a human or animal subject via a transducer, the ultrasound waves interacting with interfaces of body tissues and fluids. Contrast in an ultrasound image derives from differential reflection/absorption of the sound waves at such interfaces; results may be enhanced by the use of Doppler techniques, including the use of color Doppler to evaluate blood flow. Examples of ultrasound contrast agents include Echovist®, based on gas-containing galactose microcrystals; Levovist®, comprising gas-containing galactose microcrystals coated with fatty acid; and Infoson®, which comprises gas bubbles encapsulated by partially denatured human serum albumin.

Other imaging or diagnostic agents that may be used in the present invention include, but are not limited to, fluorescent agents such as 6-carboxyfluorescein, radioactive agents (such as radioisotopes or compounds containing radioisotopes, including iodo-octanes, halocarbons, and renografin), and the like.

In another aspect of the the invention, the liposomal preparation further comprises an additional active agent, for e.g., another chemotherapeutic drug.

EXAMPLES

Example 1

Preparation of Doxorubicin Loaded Temperature-Sensitive Liposomes by $NH_4^+$-Loading Liposomes containing 1,2-dipalmitoyl-sn-glycero-3-phosphatidyl choline (DPPC), which comprises 86% (mole %) of the liposome membrane; 1,2-distearoyl-sn-glycero-3-phosphoethanolamine-N-polyethylene glycol 2000 (DSPE-mPEG), at approximately 4% (mole %); and 1-stearoyl-2-hydroxy-sn-glycero phosphatidyl choline (MSPC) at approximately 10% (mole %) are prepared by the following technique: The appropriate lipid composition is first hydrated in 200 mM ammonium sulfate buffer, forming multi-lamellar liposomes. Small uni-lamellar liposomes are then formed by extrusion through 80 nm filters to form approximately 100 nm spheres in 200 mM ammonium sulfate buffer.

The liposomes prepared in the previous step were then subjected to a dialysis or diafiltration step exchanging the ammonium sulfate that is external to the liposome with a 10% sucrose solution, forming an ammonium concentration gradient across the liposome membrane (i.e. 200 mM inside, less than 1 mM outside). It is known (Haran G, Cohen R, Bar L K and Barenholz Y, Transmembrane ammonium sulfate gradients in liposomes produce efficient and stable entrapment of amphipathic weak bases, *Biochimica et Biophysica Acta,* 1151 (1993) 201-215 201) that the ammonium concentration can effectively, and near quantitatively, promote the loading of an added doxorubicin solution to the internal volume of the liposome at elevated temperatures. Doxorubicin was entrapped within the inner aqueous volume of the liposomes by incubation at 35-39° C. At the completion of loading, the liposomal solution was buffered with a histidine buffer to stabilize the product pH during storage.

Example 2

Preparation of pH-Loaded Temperature Sensitive Doxorubicin Liposomes

Liposomes with doxorubicin loaded using a pH gradient are prepared according to the method described in WO 2007/024826, Liposomes containing 1,2-dipalmitoyl-sn-glycero-3-phosphatidyl choline (DPPC), which comprises 86% (mole %) of the liposome membrane; 1,2-distearoyl-sn-glycero-3-phosphoethanolamine-N-polyethylene glycol 2000 (DSPE-mPEG), at approximately 4% (mole %); and 1-stearoyl-2-hydroxy-sn-glycero phosphatidyl choline (MSPC) at approximately 10% (mole %) are prepared by the following technique: The appropriate lipid composition is first hydrated in 300 mM citrate buffer (pH=4), forming multi-lamellar liposomes. Small uni-lamellar liposomes are then formed by extrusion through 80 nm filters to form approximately 100 nm spheres in 300 mM citrate buffer.

A 500 mM sodium carbonate solution is then added to the liposomes prepared in the previous step, increasing the external solution to a pH of ~7.5. It is known (see for example, Mayer L B, Bally M B, Cullis P R., Uptake of adriamyacin into large unilamellar liposomes in response to a pH gradient, *Biochimica et Biophysiea Acta* 857 (1986) 123-126) that the pH gradient formed across the membrane can effectively, and near quantitatively, promote the loading of an added doxorubicin solution to the internal volume of the liposome at elevated temperatures. Doxorubicin was entrapped within the inner aqueous volumes of liposomes by incubation at 35-39° C.

Formulation Composition/Excipients/Functionality

Table 1 displays a comparison between formulations according to Example 1, and a conventional pH loaded liposome, according to Example 2. As seen from Table 1, both formulations contain 2.0 mg/mL of doxorubicin. The formulation according to the present invention compares well to a more conventional liposomal doxorubicin formulation. All raw materials used were of pharmaceutical grade.

TABLE 1

Composition of 2.0 mg/mL Doxorubicin HCl Liposomal Product

| Ingredients | Amount/mL (mg) | | Ingredient category |
| --- | --- | --- | --- |
| | pH-Loaded | $NH_4^+$-Loaded | |
| Doxorubicin/Lipid ratio | 0.02-10 | 0.02-10 | Drug substance |
| DPPC (1,2-Dipalmitoyl-sn-glycero-3-phosphatidyl choline) | 10-50 (total lipids) | 10-50 (total lipids) | Liposomal Component |
| DSPE-PEG (1,2-Distearoyl-sn-glycero-3-phosphoethanolamine-N-polyethylene glycol 2000 | | | |

TABLE 1-continued

Composition of 2.0 mg/mL Doxorubicin HCl Liposomal Product

| | Amount/mL (mg) | | |
|---|---|---|---|
| Ingredients | pH-Loaded | $NH_4^+$-Loaded | Ingredient category |
| MSPC (1-Stearoyl-2-hydroxy-sn-glycero phosphatidyl choline) | | | |
| Lactose | 24.5 | 0-150 | Isotonic-Agent |
| Sucrose | — | 0-150 | Isotonic Agent |
| Tri-Sodium Citrate | 15.1 | — | Buffer Agent |
| Citric Acid | 14.4 | — | Buffer Agent |
| Sodium Carbonate | 13.6 | — | Buffer Agent |
| Ammonium Sulfate | — | 15-40[a] | Buffer Agent |
| Histidine | — | 0-2.0 | Buffer Agent |
| Water | QS to volume | QS to volume | Solvent |

[a]concentration of ammonium sulfate inside the liposome (e.g. 150-250 mM)

Example 3

Final Product Characterization Methods

The final product is characterized for total doxorubicin content, doxorubicin degradation products, pH, osmolality, particle size distribution, MSPC content, DPPC content, DSPE-mPEG content, % encapsulated doxorubicin, drug release at 37° C., and drug release at 41° C. to effectively complete assessment of the product. The target total doxorubicin content is between about 1.8 to about 2.2 mg/mL. The drug encapsulation was typically greater than 90%, and showed limited release, e.g. <10%, at normal body temperature (i.e. 37° C.), and exhibited enhanced release, typically >80%, at 41.0° C. The volume averaged particle size of the liposomes as measured by dynamic light scattering is between about 50 to about 150 nm.

Example 4

Physiochemical Properties

Physical Diameter of Liposomes

Figure 3:
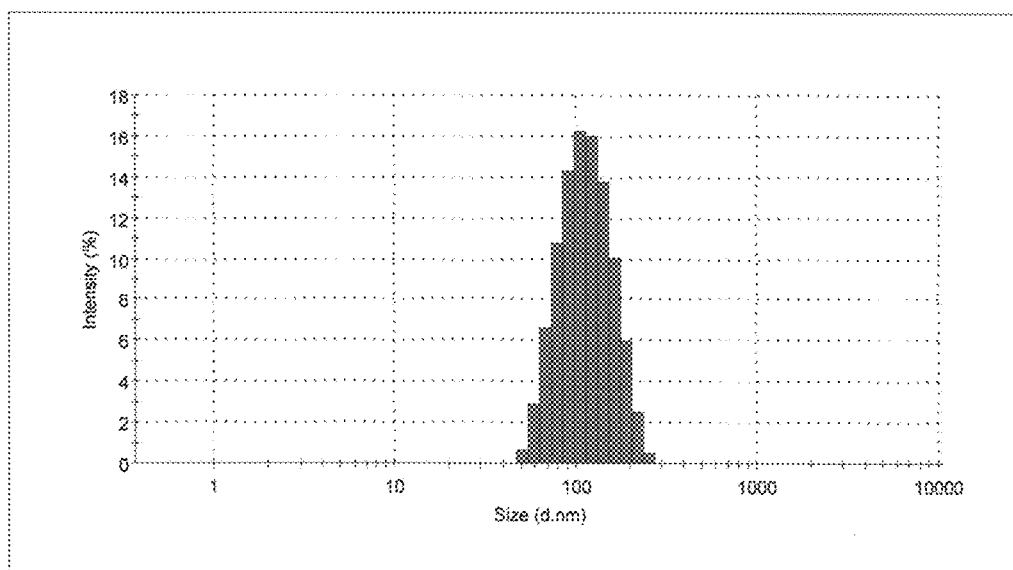
FIG. 3 is a particle size distribution of $NH_4^+$-loaded doxorubicin liposomes formed by the extrusion process.
Figure 3:
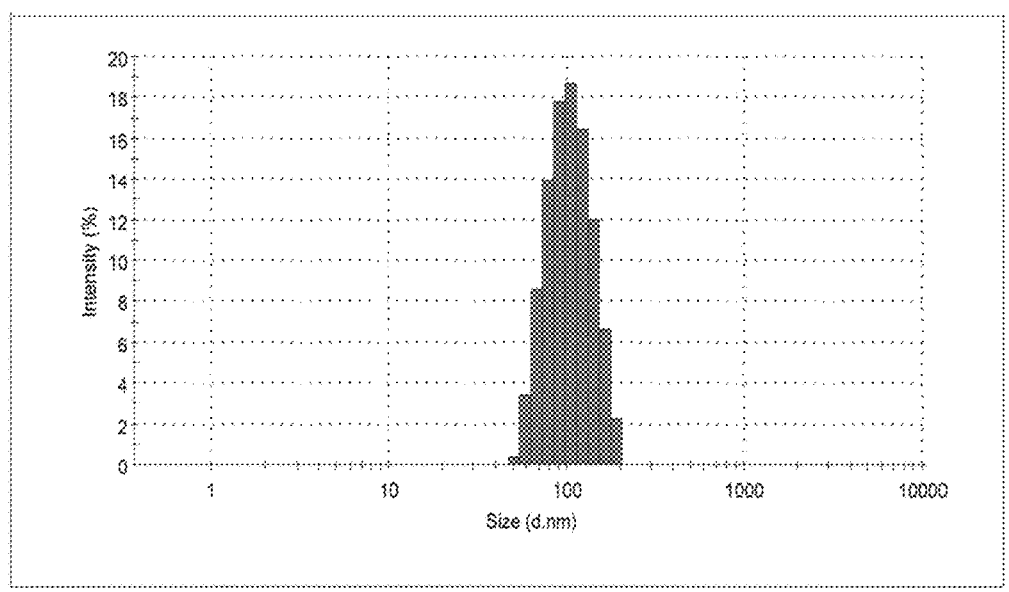

The physicochemical properties of the liposomes formed in the above Example 1 are comparable to a liposomal preparation formed using a conventional buffer. As shown in FIG. 3, the particle size distribution of ammonium sulfate hydrated liposome is essentially identical to a citrate buffer hydrated liposome.

Lipid Composition

As shown in Table 1 above, the lipid composition of the liposomal preparation of the present invention is identical to the lipid composition of the liposomal preparation known in the art. The functionality of the lipid membrane composition is also confirmed by testing the differential drug release at both 37° C. and 41.0° C.

Extent of Doxorubicin Encapsulation

The present invention provides a liposomal product designed to utilize a remote loading procedure (see for example, Haran G, Cohen R, Bar L K and Barenholz Y., Transmembrane ammonium sulfate gradients in liposomes produce efficient and stable entrapment of amphipathic weak bases, *Biochimica et Biophysica Acta*, 1151 (1993) 201-215 201), to encapsulate greater than 90% of the doxorubicin in the internal aqueous core. The % of doxorubicin encapsulated is calculated by measuring unencapsulated doxorubicin (free Dox), separated by ultrafiltration, and the total doxorubicin in the product. Current studies have shown that greater than 95% encapsulation can be achieved for the ammonium loaded formulation.

Figure 8:
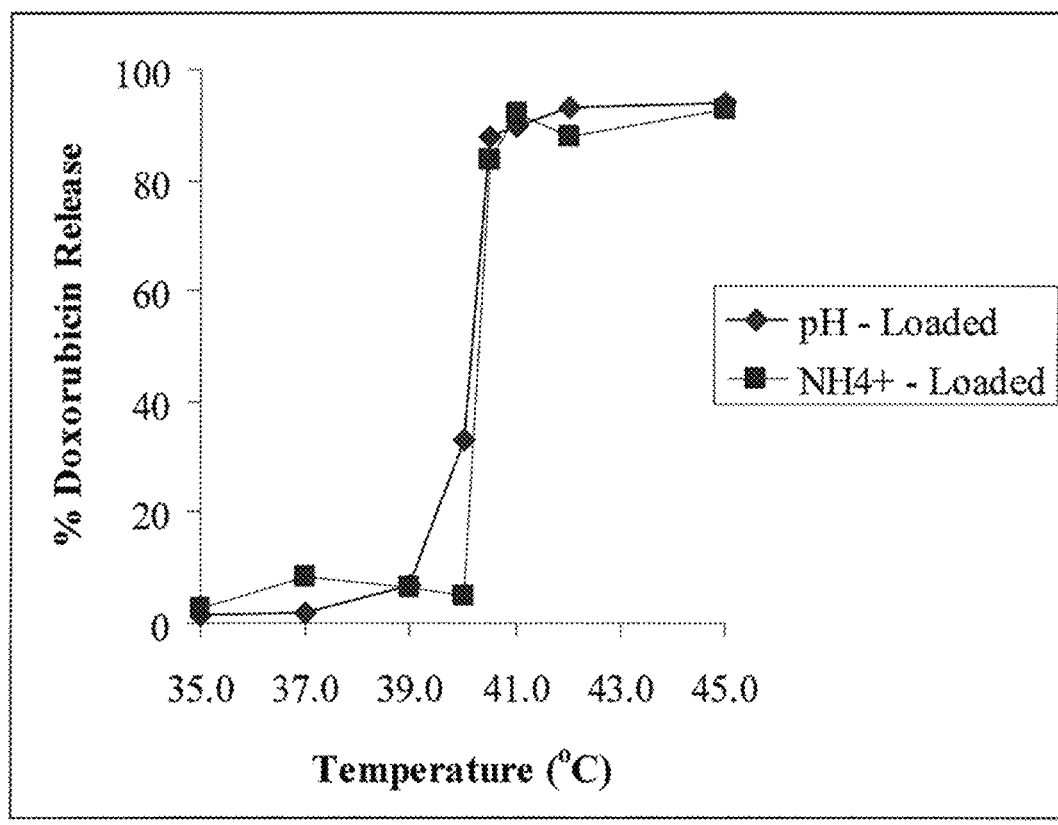
FIG. 8 shows a comparison of doxorubicin release profiles as a function of solution temperature for the pH-loaded and $NH_4^+$-loaded liposomes.

Additionally, the thermal release properties of each batch, % release at 37° C. and % release at 41° C., have been very reproducible from batch to batch, and are comparable, as shown in FIG. 8.

Final Product Characterization Methods

Figure 4:
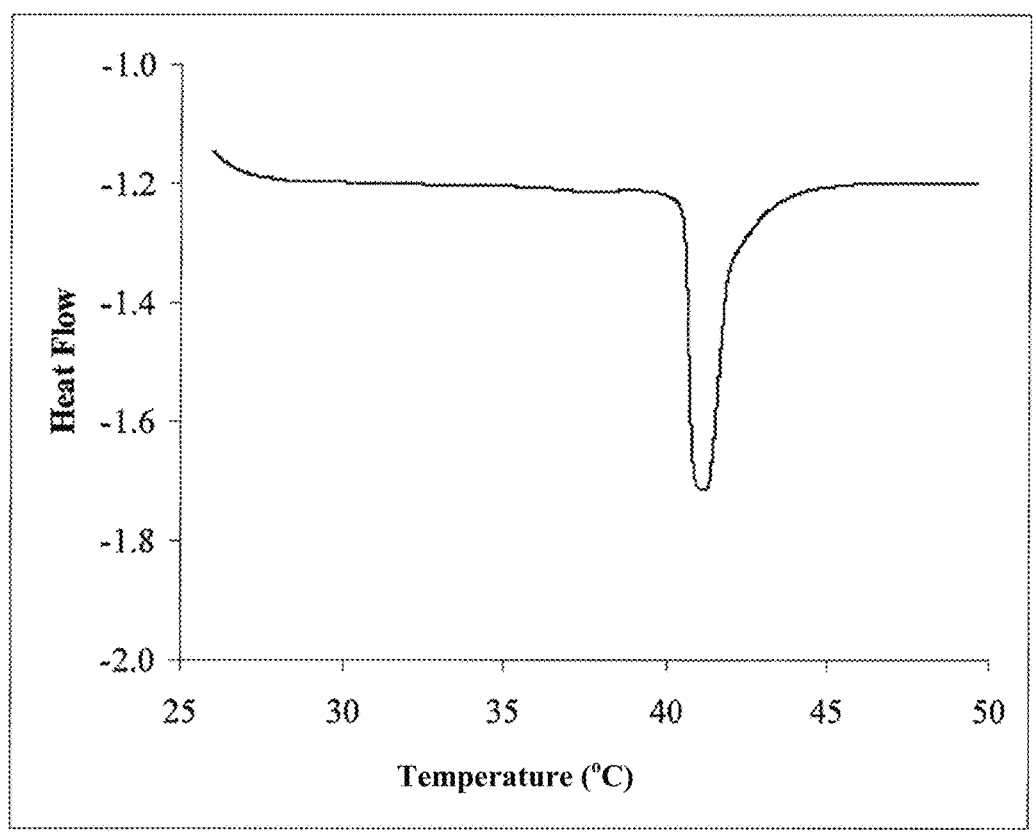
FIG. 4 depicts a differential scanning calorimetry graph (scan rate of 2° C. per minute) of pH loaded liposomes prepared using known methods in the art.
Figure 5:
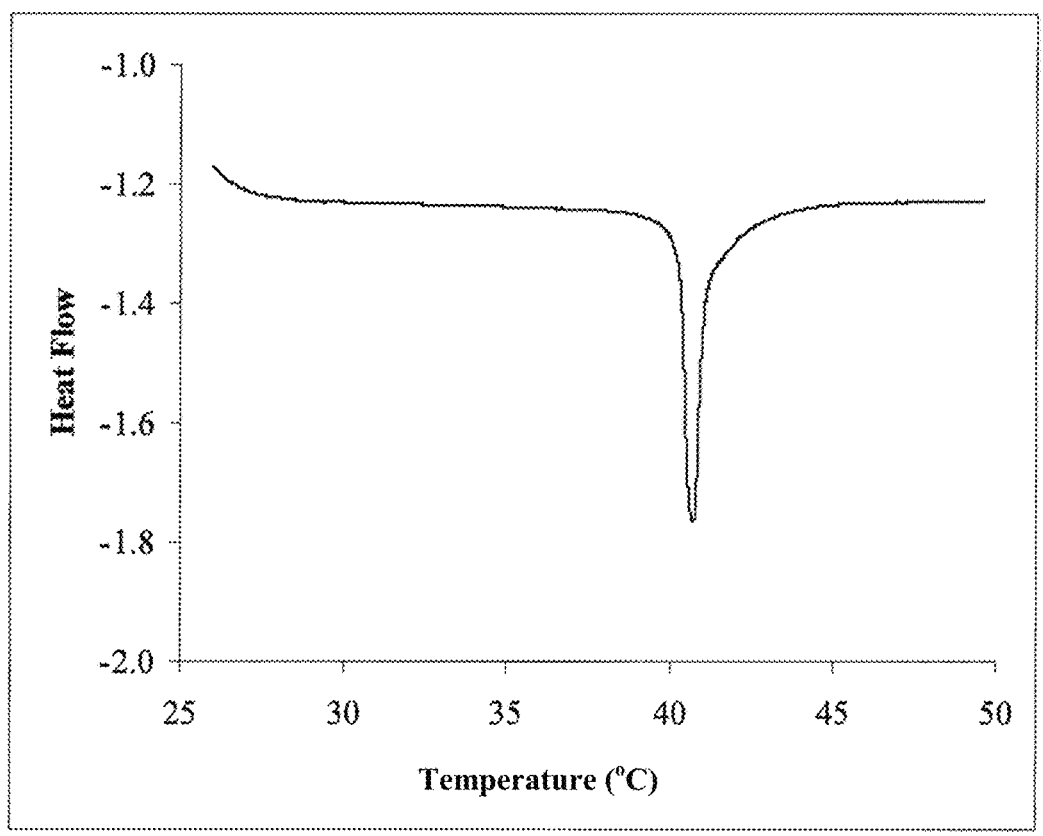
FIG. 5 depicts a differential scanning calorimetry graph (scan rate of 2° C. per minute) of $NH_4^+$-loaded liposomes of the present invention.

In addition to the list of finished product characterization tests mentioned above, several other properties of the new formulation have been evaluated. First, due to the importance of the liposome membrane in the key design parameters for the drug product, differential scanning calorimetry was performed on the pH-loaded (shown in FIG. 4) and $NH_4^+$-loaded (shown in FIG. 5) formulations. Each thermogram shows one major exotherm, at about 41° C., and suggests that the membrane for new formulation is quite similar to that for the pH-loaded liposomes, as to be expected, as the buffer solution should have negligible effects on the overall structure of the membrane order.

Figure 6:
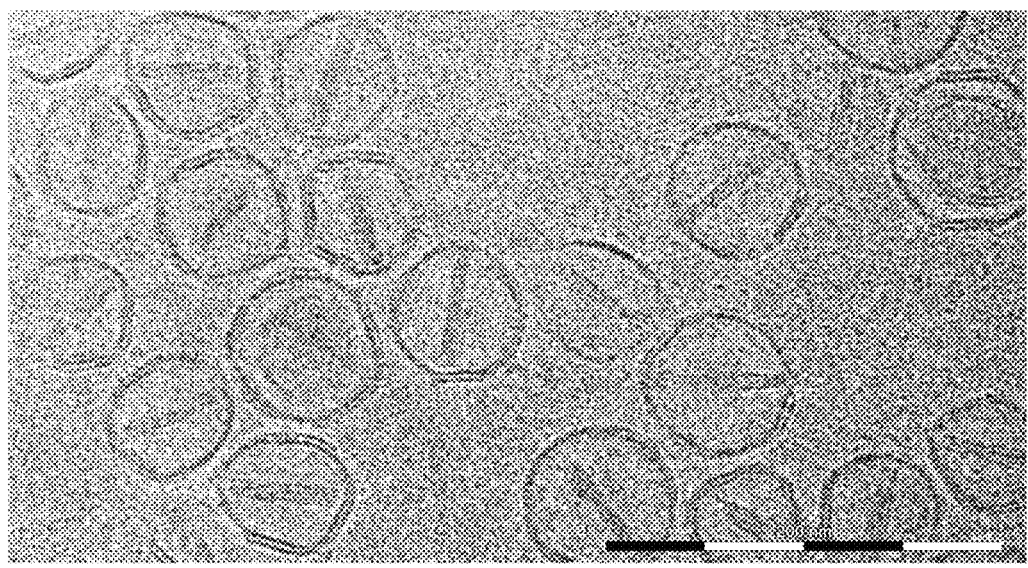
FIG. 6 depicts a tunneling electron micrograph of pH loaded liposomes prepared according to known methods in the art.
Figure 7:
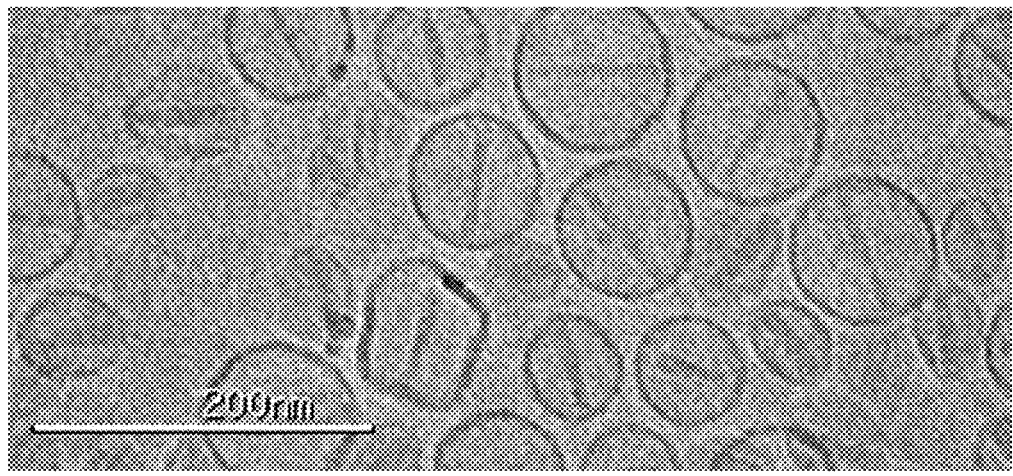
FIG. 7 depicts a tunneling electron micrograph of $NH_4^+$-loaded liposomes prepared according to the present invention.

The overall size and morphology of the two formulations were also compared using the high resolution technique of tunneling electron microscopy (TEM). Again, the comparison between pH-loaded product produced in a GMP manufacturing facility at the current manufacturing scale (FIG. 6), which is currently being used in Phase III clinical studies, to product made using the $NH_4^+$-loaded formulation at the laboratory scale at Celsion (FIG. 7) was performed. The liposomes for the two formulations show similar vesicle diameters, predominately unilamellar membranes, and exhibit a classical single crystal inside each liposome, which is attributed to the doxorubicin drug complex formation inside the liposome during the loading step. Overall, the TEMs show that the liposomes generated using either pH or $NH_4^+$-loading system are quite similar.

The temperature release profiles measuring the amount of doxorubicin released as a function of temperature from 35 to 45° C. was determined by incubating each sample at the specified temperature for 10 minutes. The results of the tests are shown in FIG. 8. As in the previous tests, the comparison was made between pH-loaded product produced in a GMP manufacturing facility at the current manufacturing scale, which is currently being used in Phase III clinical studies, to product made using the $NH_4^+$-loaded formulation at the laboratory scale at Celsion (FIG. 8). The release curves are very similar for the two formulations, both showing minimal release at temperatures below 39° C., and near 90% release at 41.0° C. and above. Clearly, both formulations support the design target of limiting doxorubicin release at normal body temperature, i.e. 37° C., with the majority of the drug being released with mild hyperthermia, or temperatures in the 41-45° C. range.

The temperature release data is also the best measure of the microscopic uniformity of the lipid membrane composition. In order for a formulation to release greater than 90% of the drug at 41.0° C., the majority of the liposomes (i.e. the 100 nm vesicles) must have the appropriate lipid composition to demonstrate the thermal triggered release for the bulk product. It is known that incorrect levels of DSPE-MPEG or MSPC will adversely affect the extent and rate of release for doxorubicin from these liposomes. Furthermore, the fact that the transition temperatures are nearly identical, in conjunction with the comparative DSC scans (FIGS. 4 and 5), leads to the conclusion that the change in the buffer system has negligible impact on liposome membrane and, therefore should have negligible impact on its drug release properties.

Example 5

Comparison of Levels of 8-Desacetyl-8-Carboxy Daunorubicin and Impurity A for the pH-Loaded and NH$_4^+$-Loaded Formulations Laboratory experiments were performed to examine the levels of 8-desacetyl-8-carboxy daunorubicin and impurity A produced in the pH-loaded and NH$_4^+$-loaded formulations (FIG. 9). Excipients sourced from two providers, excipients A and B, were examined for the pH-loaded formulation. Three independent preparations of the NH$_4^+$-loaded formulations were also examined. In all cases, and both for 8-desacetyl-8-carboxy daunorubicin and Impurity A, the levels formed were significantly higher for the pH-loaded formulations than the NH$_4^+$-loaded formulations. Reduced levels of 8-desacetyl-8-carboxy daunorubicin were observed for the pH-loaded and NH$_4^+$-loaded formulations with the new source of excipients, with no change on the levels of Impurity A.

Furthermore, the combined levels of 8-desacetyl-8-carboxy daunorubicin and Impurity A for the NH$_4^+$-loaded formulations were less than 0.2%, even with four hour incubation times at 35° C. The levels of degradate formation are shown as the initial time point in the stability data shown in FIG. 11, and correlate well with the doxorubicin values shown in FIG. 10.

Example 6

Stability Profile

Comparative stability data were generated for the pH-loaded and NH$_4^+$-loaded formulations. While the pH-loaded formulation requires storage at −15° C. to −30° C., the stability comparison was generated both at −20° C. and under accelerated stability condition, i.e., at +5° C. storage. The results of the doxorubicin assay after 739 days showed a loss of ~4% doxorubicin for the ammonium-loaded formulation. In contrast, the loss of doxorubicin after the same time period was ~60% for the pH loaded formulation. The loss of doxorubicin assay data is summarized in FIG. 10 and Table 2. The total degradate growth supports the same trend, i.e. significant increase in degradates are observed for the pH-loaded formulation, with very low levels of degradate growth for the NH$_4^+$-loaded formulation (FIG. 11 and Table 2).

TABLE 2

Stability Data for NH$_4^+$-Loaded with Storage at 2-8° C. - Doxorubicin Assay.

| Attribute | Days of Storage at 2-8° C. | | | | | | |
|---|---|---|---|---|---|---|---|
| | Initial | 21 | 35 | 77 | 175 | 362 | 739 |
| Doxorubicin (mg/mL) | 1.99 | 1.99 | 1.99 | 1.98 | 1.98 | 1.94 | 1.91 |
| pH | 6.3 | 6.3 | 6.3 | 6.3 | 6.2 | 6.1 | 6.2 |
| Particle Size (nm) | NT | 89 | 91 | 88 | 90 | 60 | 95 |
| % Encapsulation | NT | NT | 97 | 97 | 97 | 97 | 98 |
| 8-desacetyl (%) | 0.09 | 0.08 | 0.11 | 0.17 | 0.33 | 0.49 | 1.56 |
| Impurity A (%) | <0.05 | 0.12 | 0.14 | 0.18 | 0.19 | 0.42 | 0.66 |
| Total Degradates (%) | 0.09 | 0.20 | 0.25 | 0.35 | 0.52 | 0.91 | 2.22 |
| % Release at 41.0° C. | NT | NT | 90 | 88 | 87 | 89 | NT |

NT = Not Tested

In addition to the stability at 2-8° C., FIG. 12 and FIG. 13 show the loss of doxorubicin assay data at −20° C. The data demonstrate that the NH$_4^+$-loaded formulation exhibits very low levels of degradate growth and increased doxorubicin stability compared to the pH-loaded formulation.

It has also been observed that the identity of the degradation products formed from the pH-loaded and NH$_4^+$-loaded formulations are the same, confirmed by LC/MS, although formation occurs to a lesser extent for the NH$_4^+$-loaded formulation. Furthermore, the NH$_4^+$-loaded formulation exhibits improved doxorubicin HCl stability, in addition to lower levels of degradation product growth, through at least two years of storage. The solution pH, liposome particle size, % encapsulation, and % release of doxorubicin at 41.0° C. for the NH$_4^+$-loaded formulation remain through at least two years storage at temperatures of less than or equal to 8° C.

The cumulative stability data outlined above, support the assertion that the NH$_4^+$-loaded formulation can be provided commercially as a refrigerated product, stored at temperatures of less than or equal to 8° C. It is expected that the new, minimized total degrade formation will yield an acceptable product for commercial use with a shelf life of up to 2 years. The decreased degradation levels will also translate into improved maintenance of product potency. Overall, the combined effects of these improvements to the drug product are considered to enhance dosing reproducibility, achieve better shipping and storage compliance, and thus lead to a higher quality commercial product.

It is to be appreciated that the Detailed Description section, and not the Summary and Abstract sections, is intended to be used to interpret the claims. The Summary and Abstract sections may set forth one or more, but not all exemplary embodiments of the present invention as contemplated by the inventor(s), and thus, are not intended to limit the present invention and the appended claims in any way.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method for forming doxorubicin sulfate temperature sensitive liposomes, comprising:
   (a) preparing a suspension of liposomes having a gel-phase lipid bilayer and a greater concentration of ammonium and sulfate ions inside the liposomes than outside the liposomes, said lipid bilayer comprising:
      (i) one or more phospholipids that are dipalmitoylphosphatidylcholine (DPPC), distearoylphosphatidyl glycerol (DSPG) or a combination thereof;
      (ii) one or more PEGylated phospholipids; and
      (iii) one or more lysolipids selected from the group consisting of monolaurylphosphatidylcholine (MLPC), monomyristoylphosphatidylcholine (MMPC), and monostearoylphosphatidylcholine (MSPC);

wherein the lipid bilayer constituents are provided in a molar ratio of about 80-90:2-8:2-18 phospholipids: PEGylated phospholipids:lysolipids; and where said preparing includes reducing the size of the liposomes in the suspension to an average particle size of between about 50 and about 150 nm; and (b) adding a doxorubicin solution to the suspension of liposomes, wherein the doxorubicin is taken up into the liposomes in the form of doxorubicin sulfate to form doxorubicin sulfate temperature sensitive liposomes;

wherein, upon storage of the liposomes for 6 months at less than or equal to 8° C., the relative concentration of impurity A is less than 0.5%, and wherein impurity A is a peak with a relative retention time approximately 1.4 in a high performance liquid chromatography (HPLC) with a C18 reverse phase column with an acetic acid/methanol solvent gradient elution conditions.

2. The method of claim 1, wherein at least 95% of the doxorubicin present in the solution is taken up into the liposomes.

3. The method of claim 1, wherein the concentration of doxorubicin taken up into the liposomes is about 50 mM to about 75 mM.

4. The method of claim 1, wherein said preparing comprises preparing the liposomes in the presence of an ammonium sulfate solution.

5. The method of claim 4, wherein the concentration of ammonium sulfate is about 100 mM to about 300 mM.

6. The method of claim 5, further comprising replacing the ammonium and sulfate ions outside the liposomes with a monosaccharide or disaccharide solution.

7. The method of claim 6, wherein the concentration of the monosaccharide or disaccharide solution is about 5-15%.

8. The method of claim 7, wherein the ammonium and sulfate ions outside the liposomes are replaced with a monosaccharide solution.

9. The method of claim 6, wherein the ammonium and sulfate ions outside the liposomes are replaced with a disaccharide solution which is a sucrose or a lactose solution.

10. The method of claim 1, further comprising adding a histidine buffer before step (b).

11. The method of claim 10, wherein the concentration of the histidine buffer is about 5 mM to about 15 mM.

12. The method of claim 1, wherein the one or more phospholipids is dipalmitoylphosphatidylcholine, one or more PEGylated phospholipids is 1,2-distearoyl-sn-glycero-3-phosphoethanolamine-N-[poly(ethyleneglycol) 2000], and the one or more lysolipids is monostearoylphosphatidylcholine.

13. A liposome preparation made by the method of claim 1.

14. The liposome preparation of claim 13, wherein the relative concentration of impurity A after 6 months of storage at less than or equal to 8° C. is less than 0.5%, and wherein impurity A is a peak with a relative retention time approximately 1.4 in a high performance liquid chromatography (HPLC) with a C18 reverse phase column with an acetic acid/methanol solvent gradient elution conditions.

15. The liposome preparation of claim 14, wherein the relative concentration of impurity A after about 1 year of storage at less than or equal to 8° C. is less than about 0.5%.

16. The liposome preparation of claim 14, wherein the relative concentration of impurity A after about 2 years of storage at less than or equal to 8° C. is less than about 0.75%.

17. The liposome preparation of claim 13, wherein the relative concentration of 8-desacetyl-8-carboxy daunorubicin after about 1 year of storage at less than or equal to 8° C. is less than about 0.5%, or wherein the relative concentration of 8-desacetyl-8-carboxy daunorubicin after about 2 years of storage at less than or equal to 8° C. is less than about 1.6%.

18. The liposome preparation of claim 13, wherein the concentration of doxorubicin after about one year of storage at a temperature of about less than or equal to 8° C. is greater than 97% of the initial doxorubicin concentration, as determined by HPLC with a C18 reverse phase column with an acetic acid/methanol solvent gradient elution conditions.

19. The liposome preparation of claim 13, wherein the concentration of doxorubicin after about two years of storage at a temperature of about less than or equal to 8° C. is greater than 95% of the initial doxorubicin concentration, as determined by HPLC with a C18 reverse phase column with an acetic acid/methanol solvent gradient elution conditions.

20. The liposome preparation of claim 13, wherein the one or more phospholipids is dipalmitoylphosphatidylcholine, one or more PEGyated phospholipids is 1,2-di stearoyl-sn-glycero-3-phosphoethanoiamine-N-[poly(ethyleneglycol) 2000], and the one or more lysolipids is monostearoylphosphatidylcholine.

* * * * *